United States Patent
Takashima

[11] 4,131,681
[45] Dec. 26, 1978

[54] ANTIALLERGIC METHOD
[75] Inventor: Toshiyuki Takashima, Nagaokakyo, Japan
[73] Assignee: Fujisawa Pharmaceutical Co., Ltd., Osaka, Japan
[21] Appl. No.: 819,555
[22] Filed: Jul. 27, 1977
[51] Int. Cl.² .............................................. A61K 31/44
[52] U.S. Cl. ................................................... 424/267
[58] Field of Search ........................................ 424/267
[56] References Cited
U.S. PATENT DOCUMENTS
3,755,327  8/1973  Umio ................................. 260/208 C
FOREIGN PATENT DOCUMENTS
27743/1971  8/1971  Japan.

OTHER PUBLICATIONS
Fifth International Congress on Pharmacology, Jul. 23-28, 1972, San Francisco.
IX International Congress on Allergy, Oct. 28, 1976, Buenos Aires.

Primary Examiner—Stanley J. Friedman
Attorney, Agent, or Firm—Oblon, Fisher, Spivak, McClelland & Maier

[57] ABSTRACT

Compounds of the formula

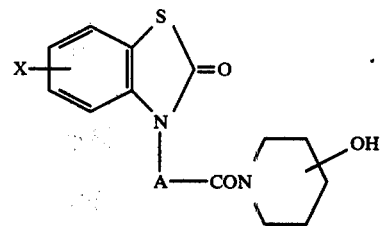

wherein A is lower alkylene and X is halogen, have been found to be useful as antiallergic agents.

5 Claims, No Drawings

ANTIALLERGIC METHOD

This invention relates to the discovery that certain 3-substituted-carbonyl(lower)alkyl-2-benzothiazolinone compounds possess antiallergic properties. These compounds are represented by the formula:

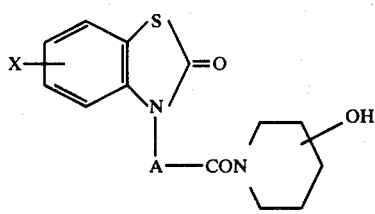

wherein A is lower alkylene and X is halogen, in which the lower alkylene group for the symbol A is exemplified with methylene, ethylene, trimethylene, propylene, tetramethylene, ethylethylene, etc., and it preferably means one having 1 to 3 carbon atom(s) and more preferably one having 1 to 2 carbon atom(s) and most preferably methylene, and halogen atom for the symbol X includes chlorine, bromine, iodine and fluorine and preferably means chlorine and bromine and most preferably chlorine, where there may be optional the positions substituted of the symbol X on the benzothiazolinone ring, preferably the 5th position, and of the hydroxy group on the piperidine ring, preferably the 3rd or 4th position and more preferably the 4th position.

This invention relates, more particularly, to use of the compound (I) as antiallergic agent for prophylaxis and therapy to mammals, to method for treating allergic diseases by administering the compound (I) itself or in a pharmaceutical form thereof and also to pharmaceutical composition useful as antiallergic agents which comprises one or more compound(s) selected from the group represented by the compound (I).

The compound (I) is known to the public by the disclosures of Japanese patent publication No. 27743/1971 and U.S. Pat. No. 3,755,327.

It is understood from the disclosures of said Japanese patent publication and USP that the compound (I) has inhibitory activity of central nervous system, antiinflammatory activity, antiarrhythmic activity and analgesic activity.

The inventor of this invention has found that the compound (I) has desirable and remarkable antiallergic activity with remarkable low toxicity and less side effects, and can be used as a drug for allergic diseases, especially asthma.

Recently, it was discovered by the inventor that tiaramide hydrochloride, 3-[4-(2-hydroxyethyl)-1-piperazinylcarbonylmethyl]-5-chloro-2-benzothiazolinone hydrochloride, has an antiallergic activity, which was presented by him at the IX International Congress of Allergy on Oct. 28, 1976 at Buenos Aires, Argentina. Tiaramide hydrochloride is an old compound which is disclosed in the above mentioned USP and Japanese patent publication No. 18752/1971 and is closely related to the compound (I) in chemical structure, though there is a difference in the substituents at the 3rd position of the benzothiazolinone ring of both compounds, that is, 4-(2-hydroxyethyl)-piperazinylcarbonylmethyl group in tiaramide hydrochloride and hydroxypiperidinocarbonylmethyl group in the compound (I).

The inventor of this invention has found that the compound (I) is more potent in antiallergic activity and lesser toxicity than tiaramide hydrochloride. Furthermore, the compound (I) does not taste bitter, while tiaramide hydrochloride is strongly bitter. No bitter taste of the compound (I) is a very advantageous property for pharmaceutical preparations in oral use, especially for children and infants.

Hitherto antiallergic drugs have been put on the market, and some of them are now practically employed for prophylactic and therapeutical purposes. However, the drugs are well known and although practically accepted still have undesirable effects and are thus inconvenient for practical use. For example, synthesized derivatives of adrenal cortical steroid hormone show typical adverse reactions which are well known to those in the art, such as mental disorders, peptic ulcer, induction and aggravation of infections (especially tuberculosis, mycosis and septicemia), adrenal cortical insufficiency, diabetes and osteoporosis, and Isoproterenol, an adrenergic $\beta$-receptor stimulant, shows an unfavorable activity on cardiovascular system, e.g., tachycardia, at the dosage administered for treatment of allergic symptoms and, in the long-term treatment with this drug, may cause suffocation because it causes an increase in the viscosity of the sputum and thus makes it more difficult for patients to cough up the accumulated sputum from the respiratory tract. Due to these undesirable properties, the above mentioned drugs have to be used under severe control of doctors or professionals.

Another antiallergic agent, disodium cromogycate, which is accepted as a desirable antiallergic drug, is not so effective when used orally, and is usually administered in the forms of injection and inhalation. The impossibility of oral administration causes inconvenience and uneasiness in practical use, especially for infants. Also, this drug is very useful for prophylactic purpose but not so useful for the so-called symptomatic treatment because it does not exert the inhibitory effect on allergic symptoms.

The inventor of this invention has further studied and found that the compound (I) can produce immediate effect and therefore it can be employed orally or parenterally for therapeutical use as well as prophylactic use, as an antiallergic agent having less side effects in a various pharmaceutical forms.

Accordingly, an object of this invention is to provide a method for utilizing the antiallergic activity of the compound (I) prophylactically or therapeutically for inhibiting or relieving symptoms associated with allergic diseases, especially bronchoconstruction in asthma.

Another object of this invention is to provide a method for treating allergic diseases to prevent or releive allergic symptoms.

Further object of this invention is to present a pharmaceutical composition useful as antiallergic agent in a pharmaceutical form for oral or parenteral use.

The compound (I) used as an active ingredient in this invention can be prepared by reacting a compound of the formula:

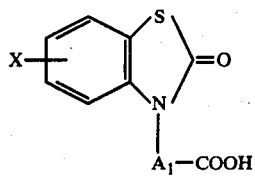

wherein $A_1$ and X are each as defined above, or its reactive derivative at the carboxy group, with a compound of the formula:

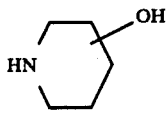

or its salt, and practical examples of preparation for some representable compounds will be given below for reference:

Preparation 1

3-(4-hydroxypiperidino)carbonylmethyl-5-chloro-2-benzothiazolinone (This compound is referred to Compound A hereinafter)

4-Hydroxypiperidine (47.2 g) was added at room temperature to and dissolved in a methanolic sodium methoxide solution prepared from sodium metal (2.2 g) in dry methanol (100 ml). To the resultant solution was added methyl 5-chloro-2-oxo-3-benzothiazolineacetate (100 g), and the mixture was heated for 3 hours under reflux with stirring. The reaction mixture was left to cool, poured into ice water (500 ml) and stirred for 30 minutes. The precipitates were collected, washed with water and then dried to give 3-(4-hydroxypiperidino)-carbonylmethyl-5-chloro-2-benzothiazolinone (102.5 g), which was recrystallized from 90% aqueous methanol to give colorless crystals, m.p. 180.1° C.

I.R. Spectrum (Nujol) 3400, 1690, 1640 $cm^{-1}$.

N.M.R. Spectrum ($d_6$-dimethylsulfoxide, $\delta$) 7.15 to 7.70 (3H, m), 4.95 (2H, s).

Preparation 2

3-(3-hydroxypiperidino)carbonylmethyl-5-chloro-2-benzothiazolinone (This compound is referred to compound B hereinafter.)

Substantially in the same manner as the above Preparation 1, were obtained crystals (21.4 g.) of Compound B. (m.p. 148 to 150° C. recrystallized from 70% hydrous methanol) from the reaction of methyl 5-chloro-2-oxo-3-benzothiazolinoneacetate (25 g) with 3-hydroxypiperidine (12.1 g).

I.R. Spectrum (Nujol) 3450, 1640, 1690 $cm^{-1}$.

N.M.R. Spectrum ($d_6$-dimethylsulfoxide, $\delta$) 7.20 to 7.75 (3H, m), 4.90 (2H, s).

The following pharmacological data are given to illustrate desirable and superior properties of the compound (I) in comparison with the well known antiallergic drugs, disodium chromoglycate (referred to Compound C hereinafter) and tiaramide hydrochloride (referred to Compound D hereinafter.)

Experiment 1

(1) Preparation of antiserum (a) Rat reaginic antiserum against egg albumin

One mg of egg albumin emulsified in 0.5 ml of B. pertussisdiphtheria mixed vaccine (Tanabe Seiyaku Company Ltd.) and 0.5 ml of Freund's incomplete adjuvant (Difco) was used as the antigen. The emulsion was given subcutaneously in a single dose of 1 ml divided equally (0.25 ml) to the four foot pads of male Sprague-Dawley JCL strain rats aged 6 weeks, each weighing 170–220 g. Blood samples were collected from the femoral artery 12 days after injection, and centifuged at 3000 r.p.m. at 4° C. for 15 minutes. The antisera thus obtained were stored at −20° C.

(b) Guinea-pig antiserum against egg albumin

Five mg of egg albumin emulsified in 0.5 ml of physiological saline and 0.5 ml of Freund's incomplete adjuvant was used as the antigen.

The amulsion was given subcutaneously in a single dose of 1 ml divided equally (0.25 ml) to the four foot pads of male Hartley strain guinea pigs, each weighing 250 to 300 g. Starting two weeks after dosing with the aforementioned emulsion, 0.1% egg albumin emulsified in physiological saline was given subcutaneously in equally divided (0.1 ml) doses of 0.4 ml once a week for 4 weeks to four sites on the backs of the test animals. Blood samples were collected from the carotid artery one week after the last injection, and centrifuged at 3000 r.p.m. at room temperature for 15 minutes. The antisera thus obtained were stored at −20° C.

(c) Rabbit antiserum against egg albumin

Fifty mg of egg albumin emulsified in 1 ml of physiological saline was used as the antigen. The emulsion was given intravenously in doses of 2 ml three times weekly for 3 weeks to male New Zealand White strain rabbits, each weighing 2 to 2.5 kg. Blood samples were collected from the carotid artery one week after the last injection, and centrifuged at 3000 r.p.m. at room temperature for 15 minutes. The antisera thus obtained were stored at −20° C.

(2) Antagonism to passive cutaneous anaphylaxis (P.C.A.) in rat

Ten male Sprague-Dawley-JCL strain rats, weighing 290–310 g, were used for each dose. The rat reaginic antiserum against egg albumin was used at a dilution 1:4. The animals were sensitized with 0.1 ml of the antiserum injected intracutaneously on the depilated backs of the rats. Fortyeight hours after the injection of the antiserum, 1 ml of mixture of egg albumin 5 mg and Evans' blue 5 mg in physiological saline 1 ml was injected intravenously. Thirty minutes after the injection of the antigen, animals were sacrificed and the skin was removed. To each sensitized area of the skin was added 10 ml of a 4:1 mixture of acetone and 2% solution of RBS-25 (Marumoto Industrial Co., Ltd.) to extract the dye and the mixture was allowed to stand for 16 hours, during of which the mixture was twice shaken for 30 minutes at 5th hour and 16th hour. It was further centrifuged at 2,000 r.p.m. for 15 minutes and the quantity of the dye in the supernatant solution was determined by colorimetry at 260 m$\mu$. Each test compound was given orally 2 hours and intravenously 5 minutes before administration of the antigen. The inhibitory effect of each test compound was determined from the dye amounts measured in comparison with the control group and the treated group and the $ED_{50}$ value was calculated according to Litchfield-Wilcoxon method.

Table 1
Inhibitory effect of P.C.A. reaction in rat

| Test Compound Administrating route & dose (mg/kg) | Inhibitory effect (%) | | | |
|---|---|---|---|---|
| | Compound A | | Compound C | |
| | p.o. | i.v. | p.o. | i.v. |
| 4 | | 22.6 | | 24.1 |
| 16 | | 41.5 | | 55.6 |
| 32 | 20.8 | | −16.1 | |
| 64 | | 49.1 | | 41.4 |
| 125 | 20.8 | | − 8.5 | |
| 500 | 62.3 | | 9.4 | |
| $ED_{50}$(mg/kg) | 348.5 | 56.6 | No effect | 73.2 |

(3) Antagonism to passive cutaneous anaphylaxis (P.C.A) in guinea-pig

Ten male Hartley strain guinea-pigs, weighing 300–350 g, were used for each dose. The animals were sensitized with 0.1 ml of the guinea-pig antiserum against egg albumin injected intracutaneously on the depilated backs of the animals. Four hours after injection of the antiserum, 1 ml of mixture of egg albumin 10 ml and Evan's blue 10 ml in physiological saline was injected intravenously. Thirty minutes after the injection of the antigen, the animals were sacrificed and the skin was removed. Each test compound was given orally 2 hours and intravenously 5 minutes before administration of the antigen. Each sensitized area of the skin was treated substantially in the same manner as that of the above mentioned test (2) to calculate $ED_{50}$ value.

Table 2
Inhibitory effect of P.C.A. reaction in guinea-pig

| Test Compound Administrating route & dose (mg/kg) | Inhibitory effect (%) | | | | | |
|---|---|---|---|---|---|---|
| | Compound A | | Compound C | | Compound D | |
| | p.o. | i.v. | p.o. | i.v. | p.o. | i.v. |
| 4 | | 15.5 | | 11.4 | | 7.4 |
| 16 | | 32.9 | | 18.4 | | 19.4 |
| 32 | 33.5 | | −25.4 | | −8.2 | |
| 64 | | 68.9 | | −2.2 | | 60.6 |
| 125 | 31.7 | | 24.6 | | 6.1 | |
| 500 | 67.4 | | − 5.6 | | 43.4 | |
| $ED_{50}$ (mg/kg) | 202.3 | 29.1 | No effect | No effect | 594.2 | 46.8 |

(4) Antagonism to anaphylactic asthma in guinea-pigs

Ten male Hartley strain guinea-pigs, weighing 270–355 g, were used for each dose. The animal was sensitized with 0.5 ml/kg of 64 fold diluted rabbit antiserum against egg albumin injected intravenously. After 24 hours, each animal was placed individually in a plastic chamber of 5.3 liter volume. An aerosol of 1% egg albumin solution was sprayed in the chamber at an average rate of 5.5 l/minute with a standard commercial nebulizer. When no death occurred within 2 hours, the animals were regarded to be protected from anaphylactic asthma. The test compounds were each given orally 1 hour before administration of the antigen. The inhibitory effect of each test compounds was determined from the number of surviving animals more than 2 hours after spray of the antigen. The $ED_{50}$ value (dose to be required 50% protection from death) was calculated according to Litchfield-Wilcoxon method.

Table 3
Inhibitory effect of anaphylactic asthma in guinea-pig

| Test Compound Dose (mg/kg) i.v. | Inhibitory effect (%) | |
|---|---|---|
| | Compound A | Compound C |
| 4 | 0 | 0 |
| 16 | 90 | 0 |
| 64 | 100 | 10 |
| $ED_{50}$(mg/kg) | About 8.5 | No effect |

(5) Antagonism to Bradykinin-induced bronchoconstruction in guinea-pigs

Ten male Hartley strain guinea-pigs were used for each dose. The animals were immobilized with an intraperitoneal dose of 100 mg/kg of gallamine. The trachea was cannulated and the lungs were dilated with air by a respiration pump at the rate of 3 ml/time and 60.2 times/minute. Bradykinin 16 mg/kg was given intravenously and bronchoconstruction induced thereby was measured by Tanbule Strain gauge according to Konzett-Rössler method. The inhibitory effect against bronchoconstruction was determined in comparison with the control group and the treated group, and the $ED_{50}$ value was measured according to Litchfield-Wilcoxon method. Each test compound was given intravenously 30 seconds before administration of the Bradykinin.

Table 4
Inhibitory effect of Bradykinin-induced bronchoconstruction in guinea-pig

| Test Compound Dose (mg/kg) i.v. | Inhibitory effect (%) | | |
|---|---|---|---|
| | Compound A | Compound C | Compound D |
| 0.064 | 12 | | −14 |
| 0.25 | 50 | | 27 |
| 1 | 89 | 12 | 44 |
| 4 | 91 | 28 | 94 |
| 16 | | 24 | 99 |
| $ED_{50}$(mg/kg) | 0.278 | >16 | 0.813 |

(6) Acute toxicity in mouse and rat

Each ten male and female ICR-JCL strain mice and Sprague-Dawley-JCL strain rats were used for each dose.

Each test compound was given to animals in a form of suspension in 0.5% methyl cellose intraperitoneally, subcutaneously and orally. After administration, the incidence of the death was recorded for successive seven days. $LD_{50}$ values were calculated by the method of Litchfield-Wilcoxon method.

Table 5

| Animal | Administrating route | Sex | $LD_{50}$ (mg/kg) Test Compound | | |
|---|---|---|---|---|---|
| | | | Compound A | Compound C | Compound D |
| Mouse | i.p. | Male | >8000 | | |
| | | Female | >8000 | | |
| | s.c. | Male | >8000* | | |
| | | Female | >8000* | | |
| | p.o. | Male | >8000 | >11000* | 564 |
| | | Female | >8000* | >11000* | 622 |
| Rat | i.p. | Male | 7110 | | |
| | | Female | 5800 | | |
| | s.c. | Male | >8000* | | |
| | | Female | >8000* | | |
| | p.o. | Male | >8000* | >11000* | 3600 |
| | | Female | >8000* | >11000* | 3800 |

*No death is observed up to that dose.

It is certainly apparent from the above data that the compound (I) shows excellent properties, that is, it is superior in antiallergic action to and lesser toxicity more than the reference compounds C and D.

In practice of the method of this invention, an effective amount of the compound (I) itself or pharmaceutical compositions thereof are administered to mammals including human beings via any of the conventional and acceptable methods known in the art.

The active ingredient of this invention can be accepted either singly or in combination with another compound or compounds selected from the group represented by the Compound (I) or other pharmaceutical agents such as analgesic agents, antibiotics, hormonal agents and the like.

The antiallergic active ingredient compound (I) can be administered via oral or parenteral route in various pharmaceutical forms such as capsules, micro-capsules, tablets, granules, powders, troches, pills, ointments, suppositories, injectable solutions, syrups, aerosols, inhalations, etc.

The antiallergic effectiveness in prophylaxis and therapy of Compound (I) is demonstrated, when administered by oral or rectal route or injection or inhalation, at varing dose ranges within the effective amount which starts about 0.25 mg/kg/day and raised upwards to a lebel below manifestation of undesirable effects, generally 200 mg/kg/day.

In topical applications such as ointment or inhalation, it is necessary to apply the active ingredient, itself or in pharmaceutical composition, to be maintained in a sufficient concentration to a designated topical part.

In prophylactic and therapeutical use, the active ingredient is employed for human beings in the following doses:

| Administration route | Dose (mg/kg/day) |
| --- | --- |
| oral | 10 to 100 |
| rectal | 50 to 200 |
| injection | 0.25 to 25 |
| (s.c. and i.m.) | 0.30 to 30 |
| inhalation | 1 to 10 | and ointment is usually administered to skin in a ratio of 100 to 2000 mg per the whole surface of back of human beings for one time application.

The administration dosages are varied considerably taken into account several conditions such as the age of the subject, the degree of prophylactic and therapeutic effect desired, etc.

In practical use, suitable amount of the active ingredient itself or pharmaceutical composition thereof is usually taken one to five time(s) a day. Among conventionally and conveniently employed forms of pharmaceutical compositions, for example, preferred dosage unit of tablets is 50, 100 or 200 mg; ampoule for injectable application in intravenous route 12.5 or 25 mg and in subcutaneous or intramuscle route 15 or 30 mg and suppository 500 mg.

The pharmaceutical compositions of this invention can contain various organic or inorganic carrier materials, which are conventionally used for pharmaceutical purpose, such as excipient (e.g. sucrose, starch, mannit, sorbit, lactose, glucose, cellose, talc, calcium phosphate, calcium carbonate, etc.), binding agent (cellose, methyl cellose, hydroxypropyl cellose, polypropylpyrrolidone, gelatin, gum arabic, polyethyleneglycol, sucrose, starch, etc.), disintegrator (e.g. starch, carboxymethyl cellose, calcium salt of carboxymethyl cellose, hydroxypropylstarch, sodium glycole-starch, sodium bicarbonate, calcium phosphate, calcium citrate, etc.), lubricant (e.g. magnesium stearate, aerosil, talc, sodium laurylsulfate, etc.), flavoring agent (e.g. citric acid, mentol, ammonium salt of grycyrlysine, glycine, orange powders, etc.), preservative (sodium benzoate, sodium bisulfite, methylparaben, propylparaben, etc.), stabilizer (citric acid, sodium citrate, acetate acid, etc.), suspending agent (e.g. methyl cellose, polyvinylpyrrolidone, aluminum stearate, etc.), dispersing agent (e.g. polysolbate 80, emalgen 408 (surface active agent), emasol (surface active agent), etc.), aqueous diluting agent (e.g. water), base wax (e.g. cacao butter, polyethyleneglycol, witepsol, white petrolatum, etc.).

The following Examples are given to illustrate this invention, but said invention is not limited thereto.

Example 1 Formula for granules or small grains

| Compound A | 500 (g) |
| --- | --- |
| Sucrose | 9250 |
| Hydroxypropyl cellose | 200 |
| Starch | 50 |

The above ingredients are blended and granulated or grained, in a conventional manner, into granules or small grains.

Example 2 Formula for capsules

| Compound A | 500 (g) |
| --- | --- |
| Starch | 1987 |
| Magnesium stearate | 13 |

The above ingredients are blended and filled in hard-gelatin-capsules, in a conventional manner, to give 10,000 capsules, each of which contains 50 mg of an active ingredient, Compound A.

Example 3 Formula for dry-syrup

| Compound A | 500 (g) |
| --- | --- |
| Sucrose | 9250 |
| Citric acid | 20 |
| Hydroxypropyl cellose | 200 |
| Sodium benzoate | 50 |

The above ingredients are blended in a conventional manner to make dry-syrup.

Example 4 Formula for tablets

| Compound A | 20000 (g) |
| --- | --- |
| Lactose | 10400 |
| Starch | 3600 |
| Ethyl Cellose | 1800 |
| Magnesium Stearate | 200 |

The above ingredients are blended and compressed, in a conventional manner, into 100,000 tablets weighing 360 mg, each of which contains 200 mg of an active ingredient, Compound A. Thus obtained tablets are, when desired, coated with sugar-coating, film-coating or enteric coating.

Example 5 Formula for tablets

| Compound A | 5000 (g) |
| --- | --- |
| Lactose | 4200 |
| Starch | 1100 |
| Ethyl cellose | 600 |

-continued

| | |
|---|---|
| Magnesium stearate | 100 |

The above ingredients are blended and compressed, in a conventional manner, into 100,000 tablets weighing 110 mg, each of which contains 50 mg of an active ingredient, Compound A. Thus obtained tablets are, when desired, coated with sugar-coating, film-coating or enteric coating.

Example 6 Formula for injectable suspension

| | |
|---|---|
| Compound A | 2500 (g) |
| Methyl cellose | 50 |
| Polyvinylpyrrolidone | 5 |
| Methyl p-oxybenzoate | 10 |
| Polysorbate 80 | 10 |
| Lidocaine hydrochloride | 50 |

The above ingredients are suspended in distilled water for injection to give injectable solution 10 l and divided to 100 ampoules, in a conventional manner, each of which contains 25% of an active ingredient, Compound A.

Example 7 Formula for suppositories

| | |
|---|---|
| Compound A | 500 (g) |
| Witepsol H12 | 1700 |

The above ingredients are blended and compressed, in a conventional manner, into 1,000 suppositories weighing 2,200 mg, each of which contains 500 mg of an active ingredient, Compound A.

Example 8 Formula for suppositories

| | |
|---|---|
| Compound A | 500 (g) |
| Polyethyleneglycol 1500 | 1275 |
| Polyethyleneglycol 4000 | 4425 |

The above ingredients are blended and compressed, in a conventional manner, into 1,000 suppositories weighing 2,200 mg, each of which contains 500 mg of an active ingredient, Compound A.

Example 9 Formula for ointments

| | |
|---|---|
| Compound A | 500 (g) |
| White petrolatum | 9025 |
| Sorbitan trioleate | 475 |

The above ingredients are blended and kneaded into ointment.

Example 10 Formula for ointments

| | |
|---|---|
| Compound A | 1000 (g) |
| White petrolatum | 8550 |
| Sorbitan trioleate | 450 |

The above ingredients are blended and kneaded into ointment.

Example 11 Formula for ointments

| | |
|---|---|
| Compound A | 5000 (g) |
| White petrolatum | 40000 |
| Sorbitan sesquioleate | 5000 |
| Cetanol | 18000 |
| Lauromacrogol | 500 |
| Butyl p-oxybenzoate | 100 |

The above ingredients are blended with distilled water and kneaded into ointment.

Example 12 Formula for Capsules for inhalation

| | |
|---|---|
| Compound A | 250 (g) |
| Lactic acid | 250 |

The above ingredients are blended and filled in 10,000 capsules of size No. 2 in a conventional manner, each of which contains 25 mg of an active ingredient, Compound A.

What we claim is:
1. A method for treating allergic diseases in mammals which comprises administering an antiallergic amount of a compound of the formula:

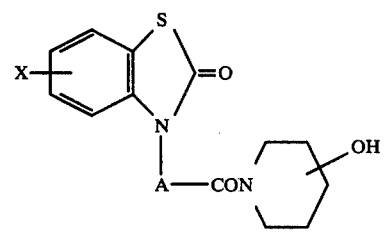

wherein A is lower alkylene and X is halogen, to said mammals.
2. The method of claim 1, wherein the compound is 3-(4-hydroxypiperidino)carbonylmethyl-5-chloro-2-benzothiazolinone.
3. The method of claim 1, wherein said compound is administered in the form of a pharmaceutical composition.
4. The method of claim 1, wherein said compound is administered in the form of a shaped medicament.
5. The method of claim 1, wherein said compound with a pharmaceutically acceptable excipient is administered in the form of granules, capsules, dry-syrup, tablets, injectable suspension, suppositories, drug for inhalation, ointment, pills, powders, or aerosols.